United States Patent [19]

Henkel et al.

[11] 4,346,112

[45] Aug. 24, 1982

[54] COMPOSITION AND METHOD FOR TREATING PATIENTS HAVING PARKINSON'S DISEASE

[75] Inventors: James G. Henkel, Manchester; Gerald Gianutsos, Tolland, both of Conn.

[73] Assignee: University Patents Inc., Norwalk, Conn.

[21] Appl. No.: 278,687

[22] Filed: Jun. 29, 1981

[51] Int. Cl.$^3$ ............................................. A61K 31/13
[52] U.S. Cl. .................................................. 424/325
[58] Field of Search ........................................ 424/325

[56] References Cited

PUBLICATIONS

Chem. Abstr. (78), (1973), 124152f.
Merck Index, 9th Ed., (1976), pp. 50–51.

*Primary Examiner*—Stanley J. Friedman
*Attorney, Agent, or Firm*—Paul J. Cook

[57] ABSTRACT

Parkinson's Disease in animals is treated by administering to the animal 3-ethyl-aminodamantane in a pharmaceutically acceptable carrier.

2 Claims, No Drawings

COMPOSITION AND METHOD FOR TREATING PATIENTS HAVING PARKINSON'S DISEASE

BACKGROUND OF THE INVENTION

This invention relates to a process for treating Parkinson's Disease and to compositions useful in such treatment.

There are presently several dopaminergic drugs either in use or being considered for use in the treatment of Parkinson's Disease, including L-DOPA, several ergot alkaloids, apomorphine derivatives and substituted 2-aminotetralins, as well as some N-substituted dopamine analogs. In one way or another, all of these compounds are based on the structure of dopamine, and most, if not all, contain the dopamine skeleton in its presumed active conformation. Based upon these rigid and semirigid agonists, as well as the structures of some confirmed dopamine antagonists, the active conformation of dopamine is now generally agreed upon. One question remaining is the exact effect of the phenyl ring hydroxyl groups. Although recent results seem to indicate that the so-called α-rotamer is the more active, others indicate that the β-rotamer also possesses activity, but in the opposite configuration. It is not yet clear if these activities are at different sites or receptors. In either case, all the drugs developed to date suffer from one or more potential clinical disadvantages, including poor absorption, inability to gain access to the central nervous system, rapid metabolic degradation, serious side effects and high toxicity.

Although the primary etiology of Parkinson's Disease remains unknown, substantial effort over two decades has produced a solid framework of knowledge regarding the processes that occur during its course. This improved state of understanding is based on advances in neurology, neurochemistry and neuropharmacology, and the resulting rational therapeutic improvements and new leads have followed from these advances.

Parkinson's Disease is now known to be based on a neurochemical defect in the nigrostriatal dopaminergic pathways of the basal ganglia, in which the dopaminergic neurons suffer severe degenerative changes. One of the consequences of these changes is the creation of a functional imbalance between the stimulatory cholinergic system and the inhibitory dopaminergic system along with changes in other subsystems, e.g., GABA. These result in the clinical symptoms of tremor, akinesia and rigidity. Even before the clinical symptoms appear, several neurochemical changes occur. As the dopaminergic neurons begin to degenerate, the activity of the remaining neurons elevates to compensate for the loss. This process is apparently mediated by several feedback mechanisms, including presynaptic and dendritic dopamine receptors (autoreceptors), the stimulation of which produces an inhibitory response in the dopaminergic neuron. This degeneration-increased activation process continues until neurohumoral balance cannot be maintained, and decomposition occurs. Along with this increased activity, postsynaptic dopamine receptor supersensitivity also develops, perhaps by way of increased receptor density. This postsynaptic adaptation likely serves to utilize the limited dopamine more effectively; it may also provide greater therapeutic access by way of an increased responsiveness to exogenous drugs directed to the postsynaptic receptor.

It has been clear for some time that dopamine receptors exist in different forms, as well as different locations in both the central nervous system and the periphery. A distinction has been made between those dopamine receptors that activate adenylylcyclase when stimulated (D1) and those that do not (D2 receptors). Both receptor types exist in more than one location, and subpopulations of each can be distinguished on the basis of their differential responses to selected agonists and antagonists. Not all of these subpopulations are relevant to Parkinson's Disease, which is known to be centered in the nigrostriatal axis. In this axis, at least five dopamine binding sites have been identified. These include a presynaptic D1 receptor intrinsic to the caudate nucleus that appears not to perform a major autoregulatory function, and a postsynaptic D1 receptor that projects to the substantia nigra. The D2 receptors include presynaptic autoreceptors that regulate dopamine neuronal activity as well as ones that affect tyrosine hydroxylase activity. The fifth receptor is a postsynaptic D2 receptor whose function is neurochemically less well described but may be that of a classic dopamine receptor. Not enough information is available to precisely define the entire process of motor regulation and the role each receptor plays. It has been proposed that Parkinson's Disease results from diminished stimulation of the postsynaptic D2 receptor, with the decompensated state arising when the autoreceptors can no longer maintain equilibrium in the systems. Therapeutic access to Parkinsonism then becomes a function of either the replacement of dopamine at the striatal (presumably D2) receptor or suitable stimulation of the receptor with some other synthetic drug. It has been suggested that the ideal agent for Parkinson's Disease should (a) have direct, full agonist action on postsynaptic dopamine receptors, (b) have transport characteristic suitable for easy access to the central nervous system (especially striatum) and (c) be metabolically stable, long lasting and with no adverse side effects. Unfortunately, such a drug does not yet exist.

However, several partial successes in the achievement of this goal have occurred, the first fully rational one being the use of L-DOPA to restore dopamine levels in the striatum. Although dopamine itself is not effectively transported into the central nervous system, its direct precursor amino acid, L-DOPA, is enzymatically decarboxylated after its facilitated central nervous system transport and uptake into the intact dopaminergic neuron and possibly other non-dopaminergic neurons. The dopamine is subsequently released into the synaptic cleft. While L-DOPA was originally expected to offer complete control of Parkinson's Disease symptoms, it is now apparent that it has serious shortcomings, including side effects. Some of these are due to the high levels of dopamine from peripheral decarboxylation of L-DOPA, while other effects are not fully explainable (dyskinesias, "on-off" syndrome). More importantly, L-DOPA becomes ineffective as the disease progresses, since it depends upon intact dopaminergic neurons for its uptake and activation. In this sense, L-DOPA acts indirectly through the intact neurons rather than directly at the postsynaptic dopamine receptor. In terms of the above ideal attributes, it is a less than ideal drug in all three areas.

Other drugs have promise as well. As a class, the ergots have been well investigated and some have reached clinical use, including bromocriptine and pergolide. These compounds appear to have mixed actions at therapeutic levels for both D1 and D2 sites. Despite some clinical success, the ergots suffer from disadvantages in several areas as antiparkinson drugs, including serious side effects caused by interactions with other (e.g., noradrenergic, serotonergic) neurotransmitter systems, low therapeutic index, and high cost. Thus, they meet only the first two of the above criteria of ideality.

Apomorphine and its derivatives have also been carefully studied, both as pharmacological tools and as potential antiparkinson drugs. The compounds are rigid congeners of dopamine and they have been shown to be both partial D1 agonists and potent D2 agonists which effectively reverse clinical Parkinsonian symptoms, although not as effectively as L-DOPA. Apomorphine is not a clinically useful drug, however, due to its short duration of action, poor oral absorption, side effects (nausea, nephrotoxicity) and metabolic instability. While congeners of apomorphine such as N-n-propyl norapomorphine seem to be therapeutically more promising, at the present time the troublesome side effects and instabilities remain.

A series currently receiving considerable attention is the catecholic 2-amino-tetralin class, or ADTN (2-aminodihydroxytetrahydronaphthalene). The 5,6- and 6,7-dihydroxy isomers (1 and 2, respectively) are semi-rigid congeners of dopamine in the extended conformation. Considerable insight into the receptor conformation of dopamine has come from these compounds as well as apomorphine, although it is not fully clear what the roles of the two phenyl

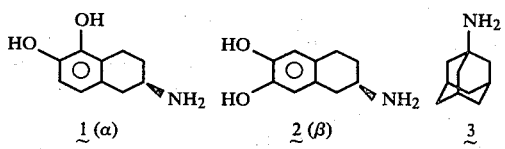

rotameric forms (α and β) are. Both 1 and 2 are dopamine agonists, with 2 being generally somewhat more potent than 1. However, the observed potencies of 1 and 2 are highly dependent on the test system used. Apparently, no clinical experience has been obtained with 1 or 2, but in animals a major drawback is an inaccessibility to the central nervous system. It is also not yet clear whether some degree of dopamine selectivity may result from restriction of rotation. The central nervous system shortcoming may be overcome by some of the more recently synthesized tertiary derivatives and prodrugs, with which side effects and metabolic stabilities may be more easily examined. In short, the ADTN series has the necessary direct dopamine agonist property, but the second and third of the above criteria await further evaluation.

While several other agents have been investigated (e.g., piribedil, a metabolically activated direct agonist, and deprenil, a selective MAO-B inhibitor), much work must be done to find agents without the troublesome side effects, metabolic instabilities and transport problems presently associated with the known direct agonists.

One clinically useful antiparkinson drug that has a nearly ideal pharmacokinetic and metabolic profile and is virtually free of side effects, is amantadine (1-aminoadamantane)3. Unfortunately, amantadine has no direct dopamine agonist activity of its own. While its exact mechanism of action is unclear, it appears to exert its weak effect indirectly by facilitating release of dopamine or hindering its uptake. The compound 3,5-dimethyl-1-aminoadamantane also exhibits antiparkinson activity but also has no direct agonist activity of its own. If one or more congeners of amantadine could be developed that has a significant direct dopamine agonist component, it would likely approach all three of the above criteria for an ideal antiparkinson drug, and hold great promise for clinical control of Parkinsonian symptoms.

SUMMARY OF THE INVENTION

The present invention is based upon the discovery that the compound 3-ethyl-1-aminoadamantane or pharmaceutically acceptable salts thereof have direct dopaminergic agonist activity. That is, the compounds utilized in this invention are not dependent upon either the production or release of dopamine in neural synapses, but acts directly on the neural receptors in the brain. All other known adamantane compounds found useful for treating Parkinson's Disease are indirect in that they act presynaptically primarily to catalyze release of dopamine.

DESCRIPTION OF SPECIFIC EMBODIMENTS

The compound, 3-ethyl-1-aminoadamantane can be prepared by the method disclosed in Czechoslovakian Pat. No. 146,405 which is incorporated herein by reference. In accordance with this invention, the compound can be administered in any pharmaceutically acceptable form. Procedures for preparing pharmaceutically acceptable salts are well known in the art. By "pharmaceutically acceptable" is meant those salt-forming compounds which do not substantially increase the toxicity of the active compound. Representative suitable salts include the hydrochloride, the hydrobromide, sulfate, phosphate, nitrate, acetate, succinate, adipate, propionate, tartrate, citrate, bicarbonate, pamoate and acetylsalicylate.

The 3-ethyl-1-aminoadamantane useful in the therapeutic method of this invention is administered to a patient afflicted with Parkinson's Disease and can be administered either alone or in combination with pharmaceutically acceptable carrier. The proportion of active ingredient to carrier is determined by the solubility and chemical nature of the 3-ethyl-1-aminoadamantane, chosen route of administration and standard pharmaceutical practice. The active compound can be administered orally, parenterally or intravenously. For example, the active compound can be administered in tablet form with such excipients as lactose, sodium citrate, calcium carbonate or dicalcium phosphate. Various disintegrants such as starch, algenic acid or certain complex silicates together with lubricating agents such as magnesium sterate, sodium aryl sulfate or talc can be utilized. For oral administration in capsule, suitable materials include lactose and high molecular weight polyethylene glycols. When utilizing aqueous suspensions, the active compound is combined with emulsifying and/or suspending agents. Diluents can be employed such as ethanol, propylene glycol, glycerine, glycine or the like. For parenteral administration, solutions of the active compound in combination with other solutes such as glucose or saline can be utilized. Such aqueous solutions should be suitably buffered in order to render them isotonic.

The dosage required to attain improvement in the undesirable effects of Parkinson's Disease, e.g., uncontrollable tremor, rigidity or akinesia is determined by the nature and extent of the progress of the disease in the patient. Generally, small dosages can be administered initially with a gradual increase in dosage until the optimal level is determined for a particular patient. When the active compound is administered orally, generally larger quantities of the active compound will be required to produce the same level of improvement of the undesirable effects as produced by a smaller quantity administered parenterally. In general from about 150 mg/day to about 450 mg/day, which is about 2 mg/day and about 7 mg/day of the active compound per kilogram of body weight administered in single or multiple dosage units effectively produces an improvement against the side effects of the disease. A particularly useful mode of administration is orally.

Unlike other adamantane compounds known to be useful in treating Parkinson's Disease, the active components of the compositions of this invention exhibit direct dopaminergic agonist activity. In contrast, the active prior art adamantane derivatives function to promote synthesis and/or release of dopamine in neuronal synapses and require the presence of dopamine. The active components of the compositions of this invention do not require the presence of dopamine in order to improve the adverse effects of Parkinson's Disease. It is highly desirable to have a drug that acts directly since, as Parkinson's Disease state progresses, the brain neurons degenerate to the point that the dopamine is depleted, thus rendering the presently available indirect agents ineffective. In addition, the active components of the compositions of this invention display ease of central nervous system penetrability and their apparently low side effects and toxicities provide substantial advantages over the prior art.

The following examples illustrate the present invention and are not intended to limit the same.

EXAMPLE I

In this example, compounds were tested for antiParkinson activity by the response to animals administered the drug in which the nigrostriatal bundle had been unilaterally lesioned by injection of 6-hydroxydopamine. These animals are considered to have an experimental unilateral Parkinsonism. These animals demonstrate a rotational behavior that is contralateral to the lesion when a directly acting dopamine agonist is administered, and an ipsilateral behavior when an indirectly acting dopamine agonist is given. The animals receiving an injection of 6-hydroxydopamine produces a destruction of the dopaminergic neurons that take up the compound producing unilateral Parkinsonism. These animals will rotate because of this striatal imbalance when injected with dopaminergic drugs.

The 3-ethyl-aminoadamantane was prepared as follows:

1-Bromo-3-ethyladamantane was prepared from 1-ethyladamantane (K. Gerzon et al, *J. Med. Chem.*, 6, 760, 1963) by stirring 0.944 grams (5.76 mmol) of 1-ethyladamantane with 10 ml of liquid bromine for 4 hours, over which time the temperature was increased to reflux. The heat was removed and after cooling, a 40 ml portion of carbon tetrachloride was added. The mixture was poured into 120 ml of ice water and enough solid sodium sulfite was added with stirring to destroy the excess bromine. The layers were separated and the aqueous phase was extracted with three portions of carbon tetrachloride. The combined extracts were washed with water, then 5% aqueous sodium bicarbonate solution, then dried over magnesium sulfate (anhydrous). Evaporation of solvent yielded a yellow liquid which was distilled to afford 1.263 grams (90.3%) of 1-bromo-3-ethyladamantane, bp 114°–115° C. (3.5 mm).

N-Acetyl-3-ethyl-1-aminoadamantane was prepared by heating 1.205 grams (4.96 mmol) of the above product with 2.95 grams (50 mmol) of acetamide at 130° C. for 4 hours. The mixture was poured into ice water and extracted four times with methylene chloride. The organic phase was washed with water, dried over anhydrous magnesium sulfate, and evaporated to give a pale yellow solid that was recrystallized from methylene chloride-petroleum ether, mp 103.5°–104.5° C.

3-Ethyl-1-aminoadamantane was prepared from the above amide by heating 858 mg (3.88 mmol) of amide with 1.5 g (39 mmol) of sodium hydroxide in 25 ml of diethylene glycol at reflux for 4 hours. After cooling, the solution was dumped into ice water and extracted four times with ethyl ether. The extracts were combined, dried over anhydrous magnesium sulfate, and evaporated to give an oil. The product was taken up in ethyl ether, to which was added a dry ethereal solution of HCl gas. The resulting solid salt was recrystallized from methylene chloride-ethyl ether to give 0.539 grams (64%) of 3-ethyl-1-aminoadamantane hydrochloride, mp 271.5°–272° C.

The 3-ethyl-aminoadamantane was compared in activity with the commercially available amantadine and compound.

Each of the aminoadamantane compounds was injected into six mice at varying dosage levels as shown in Table I. All of the aminoadamantane compounds tested induced circling behaviour, but to a varying degree. For example, amantadine was active at a dose of 0.2 mmoles/kg, but only weakly so. The most vigorous circling was produced by the 3,5-dimethyl and 3-ethyl derivatives, again at doses correlating with the motor stimulation. Of particular interest is the fact that only the 3-ethyl-aminoadamantane produce contralateral rotation (due to preferential stimulation of supersensitive receptors on the lesioned side). As expected, amantadine and memantine induced ipsilateral circling, as did the other derivatives tested, showing that they are indirect dopaminergic stimulants.

Amantadine as well as 3-methyl-aminoadamantane, 3,5-dimethyl-aminoadamantane, 3-ethyl-aminoadamantane and 3,7-dimethyl-aminoadamantane were tested against control animals and animals administered 0.01 mmoles/kg amphetamines. Animals tested with amantadine and 3-methyl aminoadamantane were given dosages of 0.2 mmoles/kg, while the remaining compounds were given to mice at levels of either 0.1 or 0.2 mmoles/kg. Prior to the administration of the test compounds, each of the mice was pretreated with 5 mg/kg reserpine plus 250 mg/kg alphamethyltyrosine (AMT). The combination of reserpine and AMT interferes with the storage and synthesis of dopamine as well as other catecholamines so that little, if any, dopamine is available for release. When analyzed, the brains of the mice from reserpine/AMT contained 80% less dopamine than control mice. Consequently, a drug which is very active in reserpine/AMT treated mice acts by an action directly on the dopamine receptor (e.g., apomorphine). The stimulation effects of amphetamine, amantadine and memantine were largely eliminated by the reserpine/AMT treatment. On the other hand, the 3-ethyl-aminoadamantane active compound of this invention showed at least about 3 times the activity of the best of the other test compounds. Thus, this test confirms that 3-ethyl-aminoadamantane acts directly on the receptors of the brain in contrast to the other aminoadamantane compounds considered to be active for the treatment of Parkinson's Disease.

TABLE I

CIRCLING IN UNILATERALLY LESIONED MICE

| Compound | Dose Mmol/Kg | Relative Activity | Direction of Rotation |
|---|---|---|---|
| Amantadine | 0.05 | 0 | — |
|  | 0.2 | ± | Ipsilateral |
| 3,5-dimethylamantadine | 0.05 | + | Ipsilateral |
|  | 0.10 | + | Ipsilateral |
| 3-ethyl-amantadine | 0.05 | + | Ipsilateral |
|  | 0.10 | + | Contralateral |
|  | 0.15 | + | Contralateral |
| 3,7-dimethyl-amantadine | 0.10 | + | Ipsilateral |

We claim:
1. The process of treating an animal afflicted with Parkinson's Disease which comprises administering to the animal between about 2 and about 7 mg/kg 3-ethyl-1-aminoadamantane in an amount effective to control the undesirable side effects of Parkinson's Disease and a pharmaceutically acceptable carrier.
2. The process of claim 1 wherein the animal is a human.